(12) United States Patent
Zhang et al.

(10) Patent No.: US 7,071,314 B2
(45) Date of Patent: Jul. 4, 2006

(54) ARYLATION METHOD FOR THE FUNCTIONALIZATION OF O-ALLYL ERYTHROMYCIN DERIVATIVES

(75) Inventors: Weijang Zhang, Grayslake, IL (US); Margaret Chi-Ping Hsu, Vernon Hills, IL (US); Anthony R. Haight, Wadsworth, IL (US); Matthew John Peterson, Gurnee, IL (US); Bikshandarkoil A. Narayanan, Mundelein, IL (US)

(73) Assignee: Abbott Laboratories, Abbott Park, IL (US)

( * ) Notice: Subject to any disclaimer, the term of this patent is extended or adjusted under 35 U.S.C. 154(b) by 395 days.

(21) Appl. No.: 10/156,404

(22) Filed: May 28, 2002

(65) Prior Publication Data

US 2003/0125531 A1   Jul. 3, 2003

Related U.S. Application Data

(60) Provisional application No. 60/294,326, filed on May 30, 2001.

(51) Int. Cl.
   *C07H 1/00*   (2006.01)
(52) U.S. Cl. ........................ 536/7.2; 536/18.5
(58) Field of Classification Search ............... 536/72, 536/7.4, 18.5, 7.2
   See application file for complete search history.

(56) References Cited

U.S. PATENT DOCUMENTS

| 4,331,803 A | 5/1982 | Watanabe et al. |
| 4,496,717 A | 1/1985 | Adachi et al. |
| 5,866,549 A | 2/1999 | Or et al. |
| 5,872,229 A | 2/1999 | Liu et al. |
| 5,919,916 A | 7/1999 | Gracey et al. |
| 5,932,710 A | 8/1999 | Liu et al. |
| 6,040,440 A | 3/2000 | Graham et al. |
| 6,075,011 A | 6/2000 | Or et al. |
| 6,124,269 A | 9/2000 | Phan et al. |

FOREIGN PATENT DOCUMENTS

| WO | 9911651 | 3/1999 |
| WO | 0078773 | 12/2000 |

OTHER PUBLICATIONS

Clark, R. F., et al., "Synthesis and Antibacterial Activity of Novel 6-0-Substituted Erythromycin A Derivatives", *Bioorganic & Med. Chem. Ltrs.*, 10:815-819 (2000).
Jeffery, T., "On the Efficiency of Tetraalkylammonium Salts in Heck Type Reactions", *Tetrahedron*, 52(30):10113-10130 (1996).
Ma, Z., et al., "Novel Erythromycin Derivatives with Aryl Groups Tethered to the C-6 Position Are Potent Protein Synthesis Inhibitors and Active against Multidrug-Resistant Respiratory Pathogens", *J. Med. Chem.*, 44:4137-4156 (1996(.

*Primary Examiner*—Elli Peselev
(74) *Attorney, Agent, or Firm*—B. Gregory Donner

(57) ABSTRACT

An efficient arylation technique for use in the synthesis of erythromycin derivatives, involving a modified Heck reaction which employs less than six mole percent of palladium catalyst and no phosphine is disclosed. With this modified Heck reaction, an O-alkenylaryl macrolide can be obtained in a much shorter reaction time than under conventional Heck reaction conditions. The modified Heck reaction can be utilized in a method for phosphine-free arylation of an O-allylic erythromycin derivative, in a method for preparing an O-alkenylaryl erythromycin A derivative, or in a method for preparing a 2', 4"-hydroxyl protected 6-O-alkenylaryl erythromycin A derivative.

12 Claims, No Drawings

ARYLATION METHOD FOR THE FUNCTIONALIZATION OF O-ALLYL ERYTHROMYCIN DERIVATIVES

This application claims priority from Provisional Application No. 60/294,326, filed May 30, 2001.

FIELD OF THE INVENTION

The present invention is directed to an efficient arylation technique for use in the synthesis of erythromycin derivatives, involving a modified Heck reaction which employs less than six mole percent of palladium catalyst and no phosphine. With this modified Heck reaction, an O-alkenylaryl macrolide can be obtained in a much shorter reaction time than under conventional Heck reaction conditions. The modified Heck reaction can be utilized in a method for phosphine-free arylation of an O-allylic erythromycin derivative, in a method for preparing an O-alkenylaryl erythromycin A derivative, or in a method for preparing a 2', 4"-hydroxyl protected 6-O-alkenylaryl erythromycin A derivative.

BACKGROUND OF THE INVENTION

Erythromycins A through D, represented by Formula I and Table 1 shown below, are well-known and potent anti-bacterial agents, used widely to treat and prevent bacterial infection.

TABLE 1

Formula I

| Erythromycin | $R^1$ | $R^2$ |
|---|---|---|
| A | —OH | —Me |
| B | —H | —Me |
| C | —OH | —H |
| D | —H | —H |

As with other anti-bacterial agents, however, bacterial strains having resistance or insufficient susceptibility to erythromycin have been identified. Also, erythromycin A has only weak activity against Gram-negative bacteria. Therefore, there is a continuing need to identify and synthesize new erythromycin-derived compounds which possess improved anti-bacterial activity, which have lower potential for developed resistance, which possess the desired Gram-negative activity, or which possess unexpected selectivity against target microorganisms.

Generally, 6-O-substituted derivatives of erythromycin are known as anti-bacterial agents. 6-O-Methyl erythromycin A (clarithromycin A, disclosed in U.S. Pat. No. 4,331,803) and 6-O-methyl erythromycin B (clarithromycin B, disclosed in U.S. Pat. No. 4,496,717) are potent macrolide antibiotics.

More recently, 6-O-substituted derivatives of erythromycin having improved antibacterial activities have been disclosed in U.S. Pat. Nos. 5,866,549; 5,872,229; 5,919,916; 5,932,710; 6,040,440; 6,075,011 and 6,124,269 among others.

Among the methods for derivatizing 6-O-allyl erythromycin derivatives is the Heck reaction, with Pd(II) or Pd(0) catalyst, phosphine and inorganic base, as disclosed in U.S. Pat. Nos. 5,866,549 and 6,075,011, and in WO 00/78773.

However, the conventional technique described above has certain disadvantages. For example, in a typical arylation of an allylic erythromycin derivative with a palladium catalyst, a phosphine and an arylating agent, yields are from 30–60%. Moreover, in the references cited above, the reactions required not less than ten mole percent of a palladium catalyst, and were conducted in the presence of an added phosphine ligand. The amount of catalyst required increases the cost of production in terms of added cost of catalyst materials, greater waste to dispose of and potential increase in contaminants to be removed from the final product. Moreover, a shorter reaction time would be advantageous.

Although both phosphine and phosphine-free conditions for Heck reactions are known in the chemical literature, phosphine-free conditions have not been utilized for macrolides such as erythromycin derivatives.

Therefore, methods for more efficient arylation would be advantageous for the construction of a 6-O-substituted side chain, which may increase the overall yield of syntheses of 6-O-substituted erythromycin derivatives. Moreover, it would be advantageous in a multi-step erythromycin derivative synthesis to form an alkene, then to arylate at a much later stage of the overall synthesis.

BRIEF SUMMARY OF THE INVENTION

The invention is directed to a method for phosphine-free arylation of an O-allylic erythromycin derivative comprising the steps of: reacting the allyl group of an O-allyl erythromycin derivative with an arylating agent in the presence of an inorganic base, a phase transfer catalyst and less than six mole percent of a palladium catalyst in an organic solvent, without addition of a phosphine, at a temperature of from about 90° C. to about 120° C. to form an O-alkenylaryleryth-romycin derivative; and then, optionally isolating said O-alkenylarylerythromycin derivative. Compounds made by this method include 6-O-(3-(3-quinolyl)-2-propen-1-yl) erythromycin A-11,12-cyclic carbamate 2', 4"-dibenzoate, 6-O-(3-(3-quinolyl)-2-propen-1-yl) erythromycin A-2', 4"-dibenzoate, 6-O-(3-(3-quinolyl)-2-propen-1-yl) erythromycin A-9-oxime-2', 4"-dibenzoate, 6-O-(3-(3-quinolyl)-2-propen-1-yl) erythromycin A-9-oxime benzoate-2', 4"-dibenzoate, 6-O-(3-(3-quinolyl)-2-propen-1-yl) erythromycin A-9-(isopropoxyl cyclohexylketal) oxime-2', 4"-dibenzoate, 6-O-(3-(3-quinolyl)-2-propen-1-yl) erythromycin A-9-(isopropoxyl cyclohexylketal) oxime-2', 4"-bis (trimethyl)silyl ether, 6-O-(3-(3-quinolyl)-2-propen-1-yl) erythromycin A-9-(diphenylphosphonimidyl)oxime 2', 4"-dibenzoate, 6-O-(3-(3-quinolyl)-2-propen-1-yl) erythromycin A-9-phenylthioimine 2', 4"-dibenzoate, 6-O-(3-(3-quinolyl)-2-propen-1-yl) erythromycin A-9-(pivaloyl)oxime 2', 4"-dibenzoate and 6-O-(3-(3-quinolyl)-2-propen-1-yl) erythromycin A-9-(isopropoxyl cyclohexylketal) oxime.

The invention is also directed to a method for preparing an O-alkenylaryl erythromycin A derivative comprising the steps of:
reacting the hydroxyl of a hydroxyl containing erythromycin A derivative with an allylating agent to form an allylic erythromycin A derivative;
reacting the allyl group of said allylic erythromycin A derivative with an arylating agent in the presence of an inorganic base, a phase transfer catalyst and less than six mole percent of a palladium catalyst in an organic solvent, without addition of a phosphine, at a temperature of from about 90° C. to about 120° C. to form an O-alkenylarylerythromycin A derivative;

and then, optionally isolating said O-alkenylarylerythromycin A derivative.

In this method, the allylating agent may be allyl t-butyl carbonate with a palladium catalyst. Compounds made by the method include 6-O-(3-(3-quinolyl)-2-propen-1-yl) erythromycin A-9-oxime benzoate-2', 4"-dibenzoate, 6-O-(3-(3-quinolyl)-2-propen-1-yl) erythromycin A-9-(isopropoxyl cyclohexylketal) oxime-2', 4"-dibenzoate, 6-O-(3-(3-quinolyl)-2-propen-1-yl) erythromycin A-9-(isopropoxyl cyclohexylketal) oxime-2', 4"-bis(trimethyl)silyl ether, 6-O-(3-(3-quinolyl)-2-propen-1-yl) erythromycin A-9-(pivaloyl) oxime 2', 4"-dibenzoate and 6-O-(3-(3-quinolyl)-2-propen-1-yl) erythromycin A-9-phenylthioimine 2', 4"-dibenzoate.

The invention is also directed to a method of preparing a 2', 4"-hydroxyl protected 6-O-alkenylarylerythromycin A derivative comprising the steps of:

protecting the 2'-hydroxyl and 4"-hydroxyl groups of a 6-hydroxyl, 2'-hydroxyl, 4"-hydroxyl erythromycin A derivative with at least one hydroxyl-protecting agent to form a 6-hydroxyl, 2', 4"-hydroxyl protected erythromycin A derivative;

allylating the C-6-hydroxyl of said 6-hydroxyl, 2', 4"-hydroxyl protected erythromycin A derivative with an allylating agent to form a 6-O-allyl, 2', 4"-hydroxyl protected erythromycin A derivative;

arylating said 6-O-allyl, 2', 4"-hydroxyl protected erythromycin A derivative with an arylating agent in the presence of an inorganic base, a phase transfer catalyst and less than six mole percent of a palladium catalyst in an organic solvent, without addition of a phosphine, at a temperature of from about 90° C. to about 120° C. to form a 2', 4"-hydroxyl protected 6-O-alkenylarylerythromycin A derivative; and then, optionally isolating said 2', 4"-hydroxyl protected 6-O-alkenylaryl erythromycin A derivative.

Subsequent to performing the method above, the 2'- and 4"-hydroxyl protected positions of said 2', 4"-hydroxyl protected 6-O-alkenylarylerythromycin A derivative may be deprotected. Compounds prepared according to this method include 6-O-(3-(3-quinolyl)-2-propen-1-yl) erythromycin A oxime 2', 4", 9-tribenzoate, 6-O-(3-(3-quinolyl)-2-propen-1-yl)-2', 4"-O-dibenzoyl erythromycin A-9-(O-isopropoxy-cyclohexylketal) oxime, 6-O-(3-(3-quinolyl)-2-propen-1-yl)-2', 4"-O-bis-trimethylsilyl erythromycin A-9-(O-isopropoxycyclohexylketal) oxime, 6-O-(3-(3-quinolyl)-2-propen-1-yl) erythromycin A-9-(O-isopropoxycyclohexylketal) oxime and 6-O-(3-(3-quinolyl)-2-propen-1-yl) erythromycin A-9-(pivaloyl)oxime 2', 4"-dibenzoate. In the method, the hydroxyl-protecting agent may be benzoic anhydride, propionic anhydride, acetic anhydride or trimethylsilyl chloride, wherein 2' and 4" positions may be protected with the same or different protecting groups. The allylating agent may be allyl t-butyl carbonate with a palladium catalyst.

For any of the methods described above, the arylating agent may be an aryl halide, wherein the aryl halide may be bromobenzene, 4-bromochlorobenzene, 4-bromopyridine, 8-bromoquinoline, 4-bromoanisole, 1-bromo-4-fluorobenzene or 3-bromoquinoline; the phase transfer catalyst may be tetrabutyl ammonium chloride, tetrabutyl ammonium bromide, tetrabutyl ammonium iodide, tetrabutyl ammonium sulfate or a combination thereof; the palladium catalyst may be palladium (II) acetate, palladium (II) chloride, palladium dibenzylideneacetone, dichlorobis(acetonitrile) palladium (II), dichlorobis(benzonitrile)palladium (II), dichlorodiamine palladium (II), palladium (II) acetylacetonate, palladium (II) bromide, palladium (II) cyanide, palladium (II) iodide, palladium oxide, palladium (II) nitrate hydrate, palladium (II) sulfate dihydrate, palladium (II) trifluoroacetate, tetraamine palladium (II) tetrachloropalladate, tetrakis(acetonitrile)palladium (II) tetrafluoroborate or a combination thereof, the organic solvent may be dimethoxyethane, acetonitrile, N,N-dimethylformamide, N,N-dimethylacetamide, 1,3-dimethyl-3,4,5,6-tetrahydro-2 (1H)-pyrimidinone, N-methylpyrrolidone, toluene, tetrahydrofuran or a combination thereof; and the inorganic base may be $K_2CO_3$, KOAc, NaOAc, $Li_2CO_3$, $LiHCO_3$, $Ag_2CO_3$, $Cs_2CO_3$, $KHCO_3$, $K_2CO_3$, $Na_2CO_3$ or $NaHCO_3$.

The invention is also directed to a method for phosphine-free arylation of 6-O-propenyl erythromycin A comprising the steps of: reacting the allyl group of 6-O-propenyl erythromycin A with 3-bromoquinoline in the presence of sodium bicarbonate, tetrabutyl ammonium chloride and less than six mole percent of $Pd(OAc)_2$ in N,N-dimethylformamide, without addition of a phosphine, at a temperature of from about 90° C. to about 120° C. to form 6-O-(3-(3-quinolyl)-2-propen-1-yl) erythromycin A; and then, optionally isolating 6-O-(3-(3-quinolyl)-2-propen-1-yl) erythromycin A.

The invention is also directed to a method for a single pot allylation and arylation of erythromycin A comprising the steps of:

reacting the 6-hydroxyl of erythromycin A with allyl t-butyl carbonate and a palladium catalyst to form 6-O-propenyl erythromycin A;

reacting the allyl group of 6-O-propenyl erythromycin A with 3-bromoquinoline in the presence of sodium bicarbonate, tetrabutyl ammonium chloride and less than six mole percent of $Pd(OAc)_2$ catalyst in N,N-dimethylformamide, without addition of a phosphine, at a temperature of from about 90° C. to about 120° C. to form 6-O-(3-(3-quinolyl)-2-propen-1-yl) erythromycin A; and then, optionally isolating 6-O-(3-(3-quinolyl)-2-propen-1-yl) erythromycin A.

The invention is also directed to a method of preparing 6-O-(3-(3-quinolyl)-2-propen-1-yl) erythromycin A-2', 4"-dibenzoate comprising the steps of: protecting the 2'-hydroxyl and 4"-hydroxyl groups of erythromycin A with benzoic anhydride to form erythromycin A 2', 4"-dibenzoate; allylating the C-6 hydroxyl of erythromycin A 2', 4"-dibenzoate with allyl t-butyl carbonate and a palladium catalyst to form 6-O-propenyl erythromycin A 2', 4"-dibenzoate;

arylating 6-O-propenyl erythromycin A 2', 4"-dibenzoate with 3-bromoquinoline in the presence of sodium bicarbonate, tetrabutyl ammonium chloride and less than six mole percent of $Pd(OAc)_2$ catalyst in N,N-dimethylformamide, without addition of a phosphine, at a temperature of from about 90° C. to about 120° C. to form 6-O-(3-(3-quinolyl)-2-propen-1-yl) erythromycin A-2', 4"-dibenzoate; and then, optionally isolating 6-O-(3-(3-quinolyl)-2-propen-1-yl) erythromycin A-2', 4"-dibenzoate.

DETAILED DESCRIPTION OF THE INVENTION

Definitions of Terms

The term "alkyl" as used herein, alone or in combination, refers to $C_1$–$C_{12}$ straight or branched, substituted or unsubstituted saturated chain radicals derived from saturated hydrocarbons by the removal of one hydrogen atom, unless the term alkyl is preceded by a $C_x$–$C_y$ designation. Representative examples of alkyl groups include methyl, ethyl, n-propyl, iso-propyl, n-butyl, sec-butyl, iso-butyl, and tert-butyl among others.

The term "alkenyl" as used herein, alone or in combination, refers to a substituted or unsubstituted straight-chain or substituted or unsubstituted branched-chain alkenyl radical containing from 2 to 10 carbon atoms. Examples of such radicals include, but are not limited to, ethenyl, 2-propenyl, E- and Z-pentenyl, decenyl and the like.

The term "allyl" as used herein, refers to a —$CH_2$—$CH$=$CH_2$ functional group.

The term "lower" modifying "alkyl", "alkenyl", "alkynyl" or "alkoxy" refers to a $C_1$–$C_6$ unit for a particular functionality. For example lower alkyl means $C_1$–$C_6$ alkyl.

The term "aryl" or "aromatic" as used herein alone or in combination refers to a substituted or unsubstituted carbocyclic aromatic group having about 6 to 12 carbon atoms such as phenyl, naphthyl, indenyl, indanyl, azulenyl, fluorenyl and anthracenyl; or a heterocyclic aromatic group which is an aromatic ring containing at least one endocyclic N, O or S atom such as furyl, thienyl, pyridyl, pyrrolyl, oxazolyl, thiazolyl, imidazolyl, pyrazolyl, 2-pyrazolinyl, pyrazolidinyl, isoxazolyl, isothiazolyl, 1,2,3-oxadiazolyl, 1,2,3-triazolyl, 1,3,4-thiadiazolyl, pyridazinyl, pyrimidinyl, pyrazinyl, 1,3,5-triazinyl, 1,3,5-trithianyl, indolizinyl, indolyl, isoindolyl, 3H-indolyl, indolinyl, benzo[b]furanyl, 2,3-dihydrobenzofuranyl, benzo[b]thiophenyl, 1H-indazolyl, benzimidazolyl, benzthiazolyl, purinyl, 4H-quinolizinyl, isoquinolinyl, cinnolinyl, phthalazinyl, quinazolinyl, quinoxalinyl, 1,8-naphthridinyl, pteridinyl, carbazolyl, acridinyl, phenazinyl, phenothiazinyl, phenoxyazinyl, pyrazolo[1,5-c]triazinyl and the like. "Arylalkyl" and "alkylaryl" incorporate the terms "alkyl" and "aryl" as defined above. "Alkenylaryl" incorporates the terms "alkenyl" and "aryl" as identified above. Rings may be multiply substituted.

The term "cycloalkyl" as used herein refers to an aliphatic ring system having 3 to 10 carbon atoms and 1 to 3 rings, including, but not limited to cyclopropyl, cyclopentyl, cyclohexyl, norbornyl, and adamantyl among others. Cycloalkyl groups can be unsubstituted or substituted with one, two or three substituents independently selected from lower alkyl, haloalkyl, alkoxy, thioalkoxy, amino, alkylamino, dialkylamino, hydroxy, halo, mercapto, nitro, carboxaldehyde, carboxy, alkoxycarbonyl and carboxamide.

"Cycloalkyl" includes cis or trans forms. Furthermore, the substituents may either be in endo or exo positions in the bridged bicyclic systems.

The term "hydroxyl" as used herein, refers to —OH.

"Hydroxy protecting group" as used herein, refers to an easily removable group known in the art to protect a hydroxyl group against undesirable reaction during synthetic procedures, which can then be selectively removed. The use of hydroxy protecting groups is well known in the art, and is described in detail in *Protective Groups in Organic Synthesis*, 3rd Edition, by T. Greene and P. Wuts, published by John Wiley & Sons in New York in 1999. Examples of hydroxy protecting groups include, but are not limited to, methylthiomethyl, tert-dimethylsilyl, acetate, benzoate, propionate, trimethylsilyl and tert-butyldiphenylsilyl among others.

The term "protected hydroxy" refers to a hydroxy group protected with a hydroxy protecting group, as defined above, such as benzoyl, acetyl, propionyl, trimethylsilyl, triethylsilyl or methoxymethyl groups, among others.

The term "halide" as used herein, refers to —I, —Br, —Cl or —F.

"Nitrogen-protecting group" as used herein, refers to an easily removable group known in the art to protect a nitrogen group against undesirable reaction during synthetic procedures, which can then be selectively removed. The use of nitrogen protecting groups is well known in the art, and is described in detail in *Protective Groups in Organic Synthesis*, 3rd Edition, by T. Greene and P. Wuts, published by John Wiley & Sons in New York in 1999. Examples of nitrogen protecting groups include, but are not limited to, carbamates, amides, aryls and enamines, among others.

The term "phosphine" as used herein, refers to compounds of the structure $(R^r)_3P$, wherein $R^r$ is an alkyl or aryl group, as defined above.

The term "phosphine-free" as used herein, refers to a reaction performed in the absence of phosphine, as defined above.

Use of the above terms is meant to encompass substituted and unsubstituted moieties. Substitution may be by one or more groups such as alcohols, ethers, esters, amides, sulfones, sulfides, hydroxyl, nitro, cyano, carboxy, amines, heteroatoms, lower alkyl, lower alkoxy, lower alkoxycarbonyl, alkoxyalkoxy, acyloxy, halogens, trifluoromethoxy, trifluoromethyl, alkyl, aralkyl, alkenyl, alkynyl, aryl, cyano, carboxy, carboalkoxy, carboxyalkyl, cycloalkyl, cycloalkylalkyl, heterocyclyl, alkylheterocyclyl, heterocyclylalkyl, oxo, arylsulfonyl and aralkylaminocarbonyl or any of the substituents of the preceding paragraphs or any of those substituents either attached directly or by suitable linkers. The linkers are typically short chains of 1–3 atoms containing any combination of —C—, —C(O)—, —NH—, —S—, —S(O)—, —O—, —C(O)O— or —S(O)O—. Rings may be substituted multiple times.

The terms "erythromycin derivative" or "erythromycin derivatives" refer to erythromycins A-D (shown in Formula I and Table 1) and derivatives thereof. Derivatives include substitutions for the C-2–C-13 hydrogen, hydroxy, alkyl or alkoxyl substituents of erythromycins A-D, with different hydrogen, hydroxy, alkyl or alkoxyl substituents. Other examples of useful erythromycin derivatives are disclosed in U.S. Pat. Nos. 5,866,549; 5,872,229; 5,919,916; 5,932,710; 6,040,440; 6,075,011 and 6,124,269, the disclosures of which are hereby incorporated by reference.

Abbreviations

Abbreviations which have been used in the schemes and the examples which follow are: Bz for benzoyl; Me for methyl; Ac for acetyl, Ph for phenyl; equiv for equivalents; conc. for concentrated; DMF for N,N-dimethyl formamide; EtOAc for ethyl acetate; TBACl for tetrabutyl ammonium chloride; IPAc for isopropyl acetate; NaHMDS for sodium hexamethyldisilazane; BrQuin for 3-bromoquinoline; FR for flow rate; min. for minutes; % PA for percent peak area; TLC for thin layer chromatography; HPLC for high pressure liquid chromatography; LC-MS for liquid chromatography-mass spectroscopy; MW for molecular weight; dppf for diphenylphosphinoferrocene, dppb for 1,4-bis(diphenylphosphino)butane and dba for dibenzylideneacetone.

Aspects of the methods of the present invention are presented in the following Schemes. Scheme 1 shows the construction of an alkene on an erythromycin derivative, in preparation for arylation. Such alkene formation is disclosed in WO 00/78773.

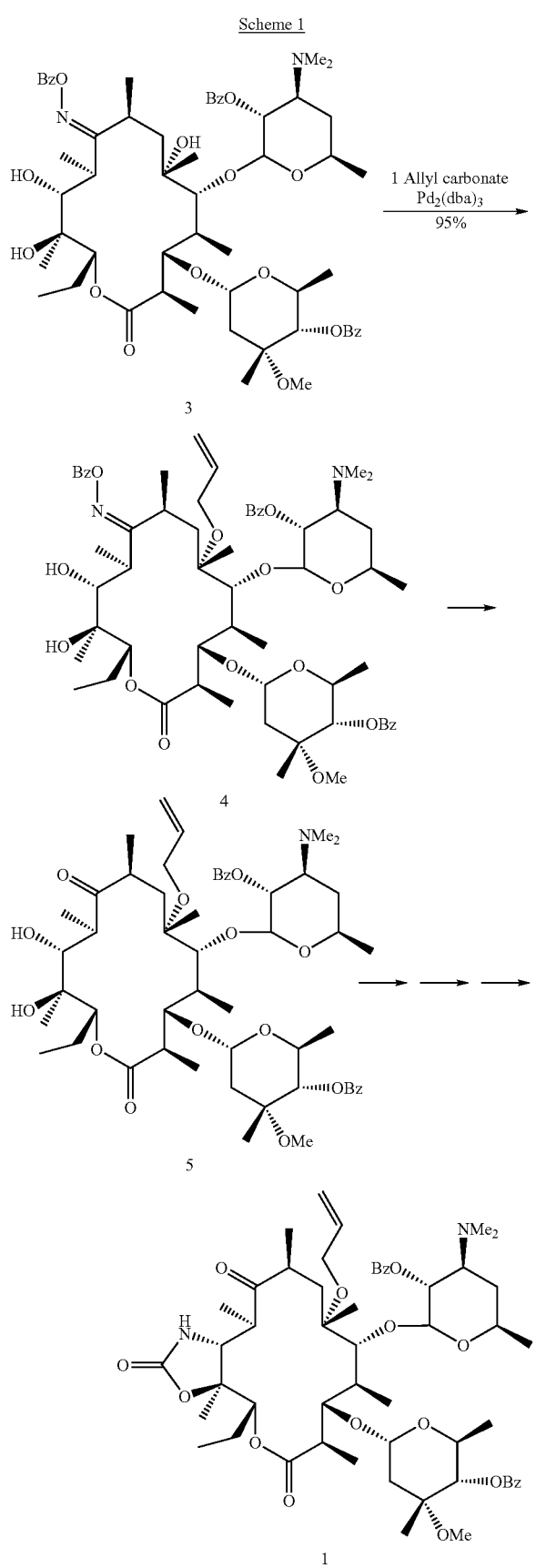
Scheme 1
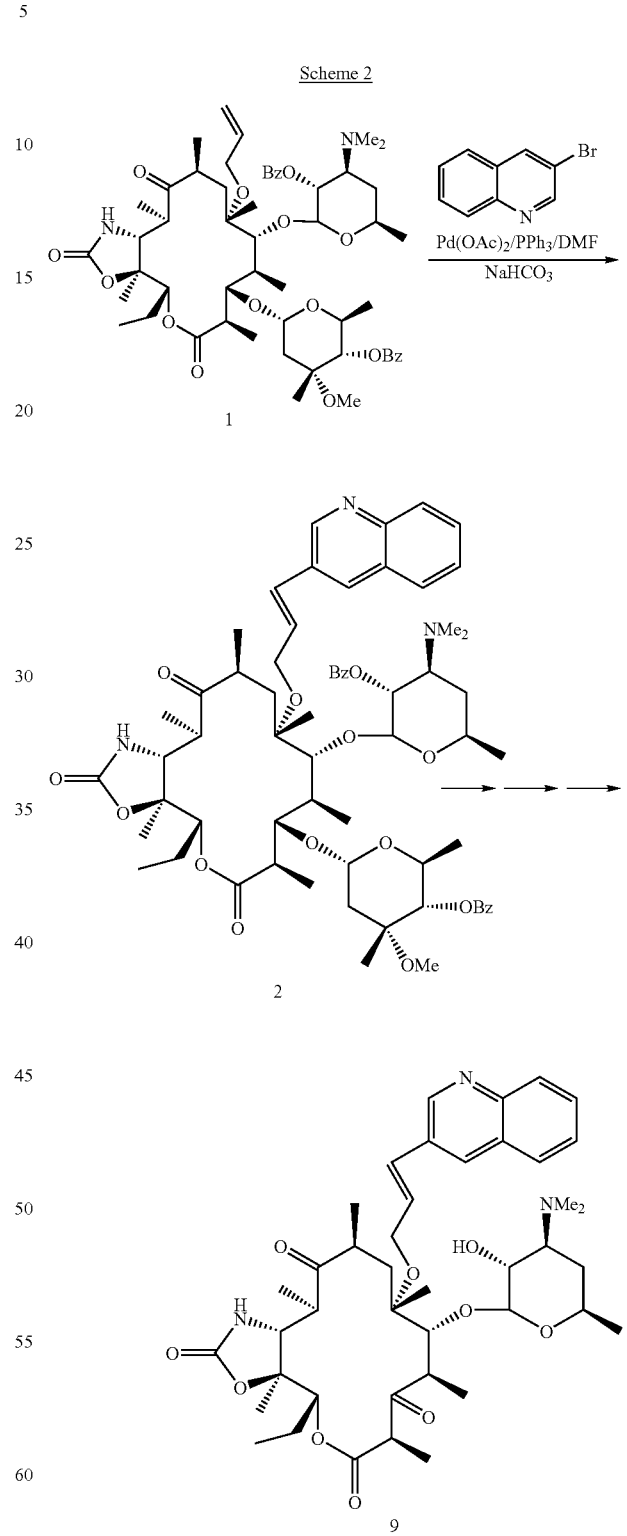
Scheme 2 shows a conventional arylation (employing a phosphine) used in formation of a 6-O-alkenylaryl erythromycin derivative, from the alkene formed as in Scheme 1, above.
Scheme 2
Scheme 3, shown below, illustrates the procedure of Example 1, a phosphine-free arylation of an alkene-containing erythromycin derivative.

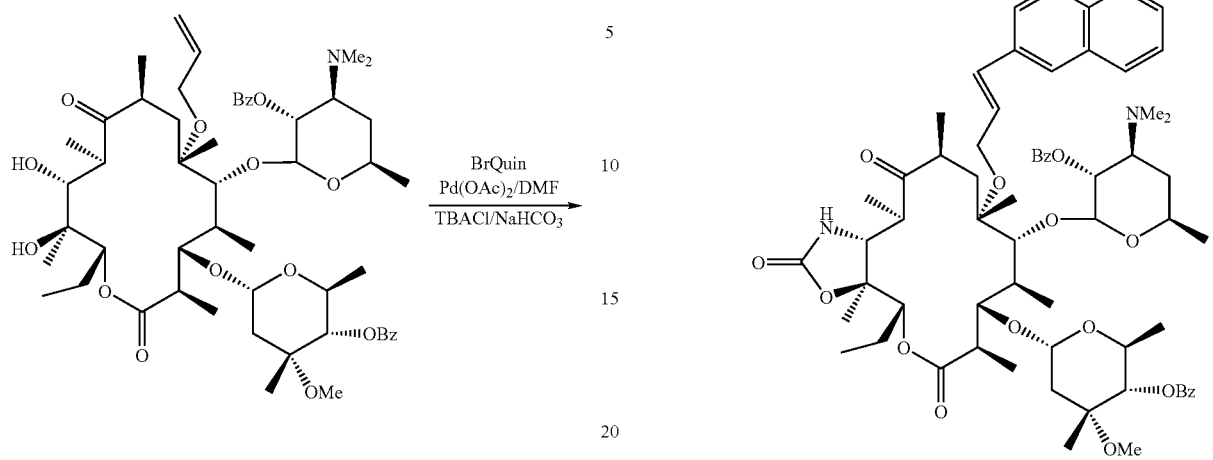
Scheme 5, shown below, illustrates the procedure of Example 3, another phosphine-free arylation of an alkene-containing erythromycin derivative.

The reaction illustrated in Scheme 5 above was also performed upon compounds C—F, shown below.
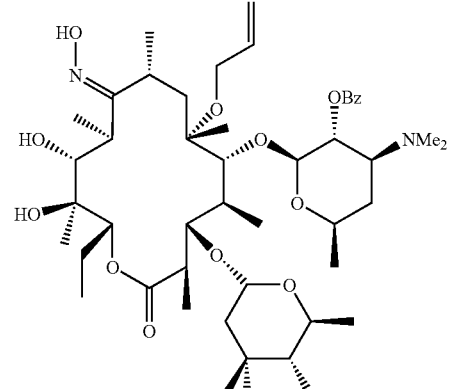
C
$C_{54}H_{80}N_2O_{15}$
Mol. Wt: 997.2
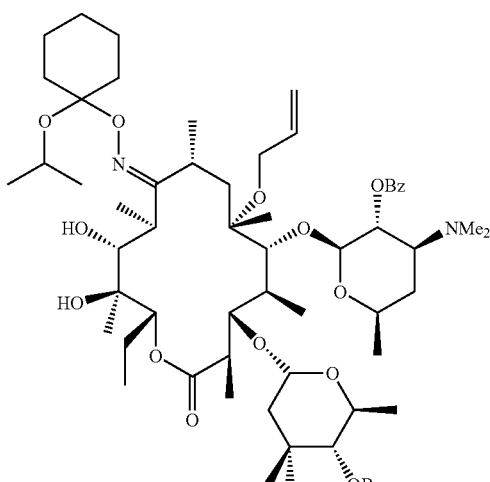
D
$C_{63}H_{96}N_2O_{16}$
Mol. Wt: 1137.4
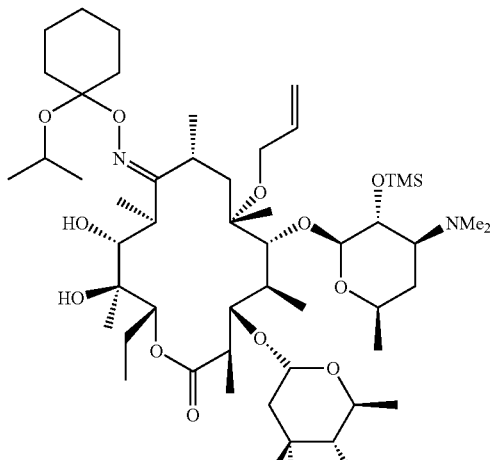
E
$C_{55}H_{104}N_2O_{16}Si_2$
Mol. Wt: 1073.6
-continued
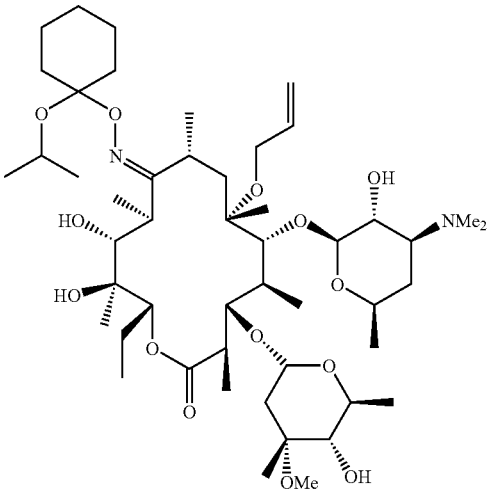
F
$C_{49}H_{88}N_2O_{14}$
Mol. Wt: 929.2
Scheme 6, shown below, illustrates the procedure of Example 4, preparation of starting material macrolide phosphoimide 2 from macrolide 1, in preparation for phosphine-free arylation of 2.
Scheme 6
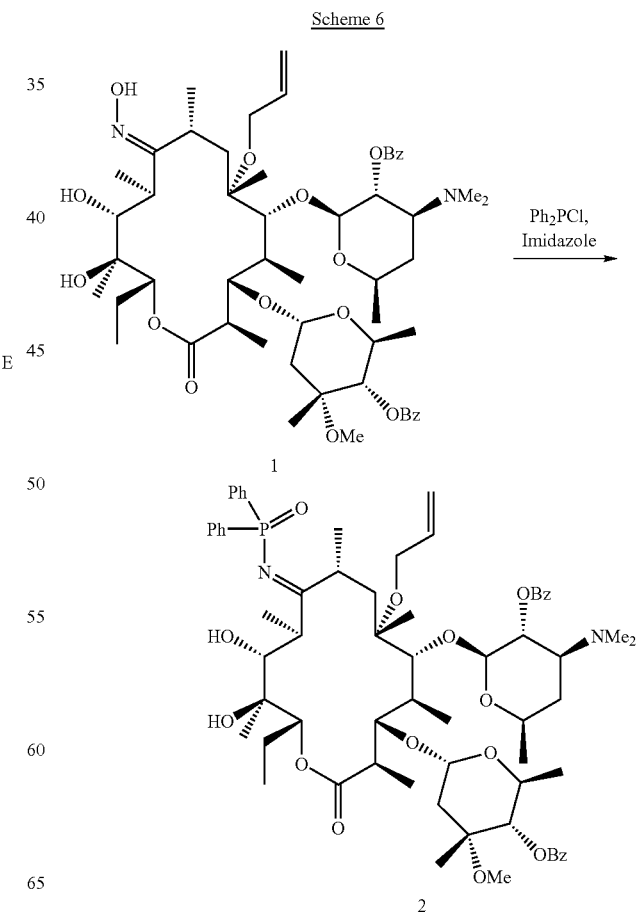

Scheme 7, shown below, illustrates the procedure of Example 5, a phosphine-free arylation of macrolide phosphoimide 2.

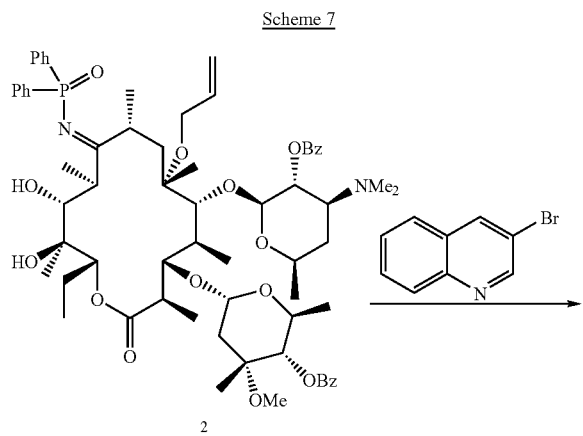

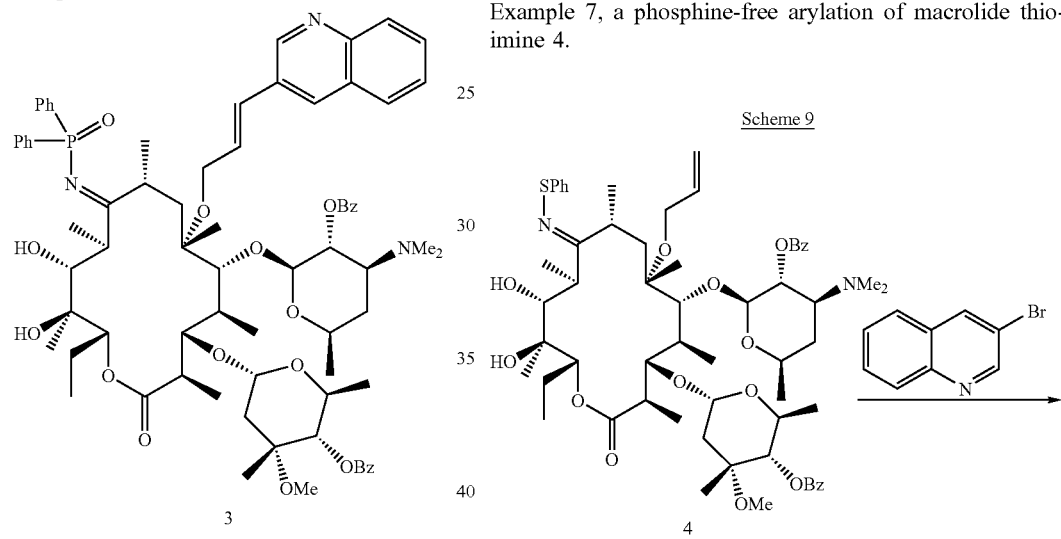

Scheme 8, shown below, illustrates the procedure of Example 6, preparation of starting material macrolide thioimine 4 from macrolide 1, in preparation for phosphine-free arylation of 4.

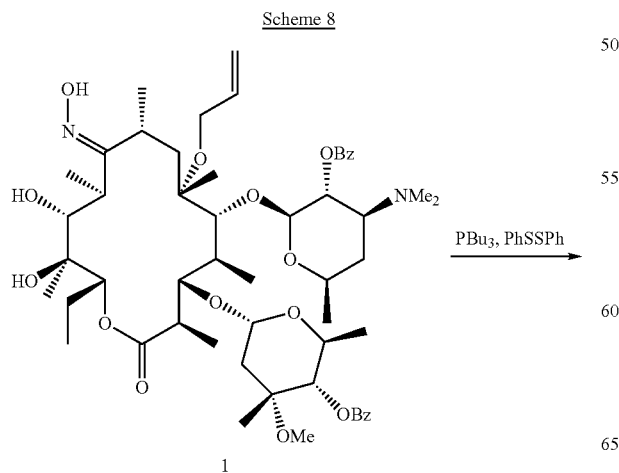

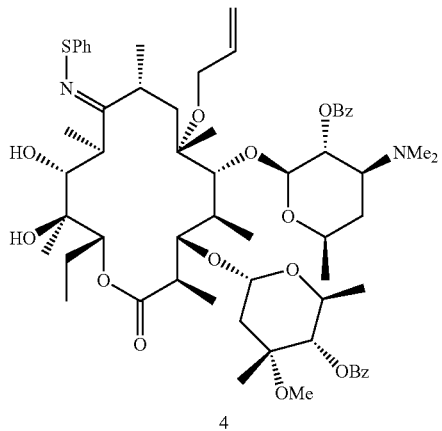

Scheme 9, shown below, illustrates the procedure of Example 7, a phosphine-free arylation of macrolide thioimine 4.

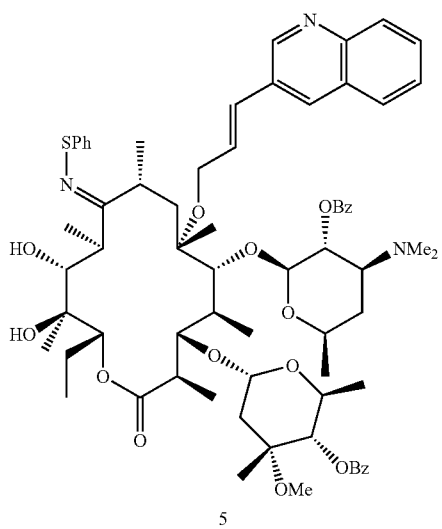

Scheme 10, shown below, illustrates the procedure of Example 8, a single pot phosphine-free arylation.

Scheme 10
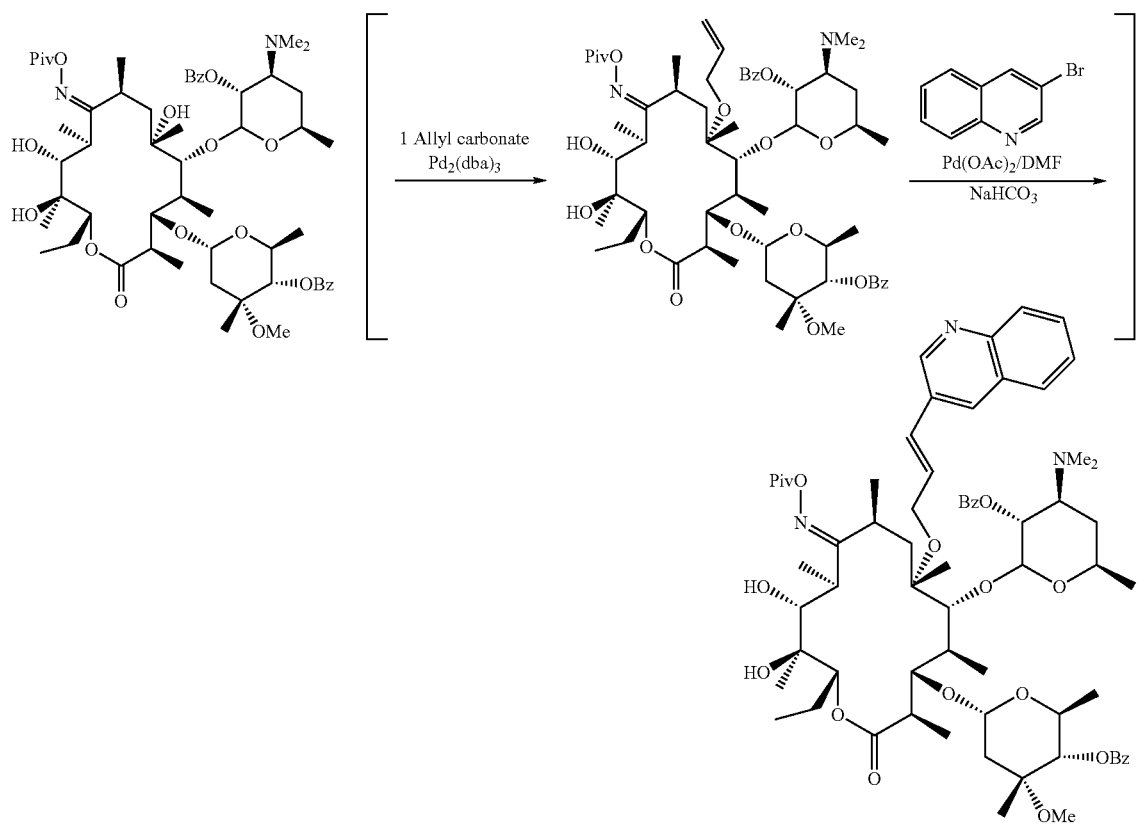
Scheme 11, shown below, illustrates the procedure of Example 9, another single pot phosphine-free arylation.
Scheme 11
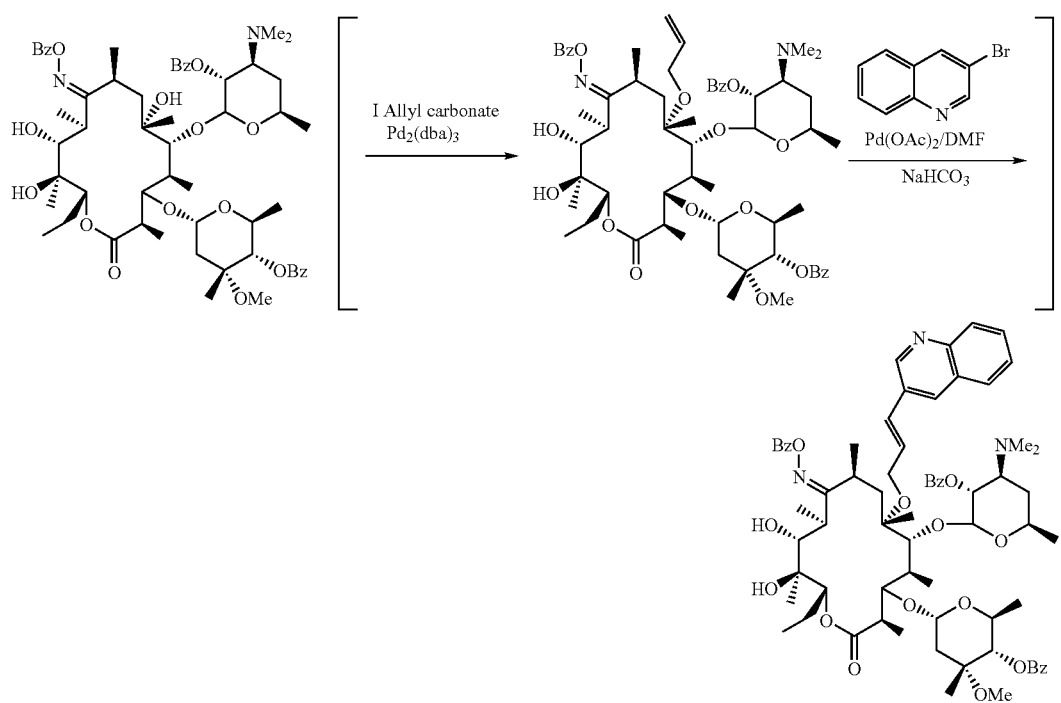

The present invention is directed to an efficient arylation technique for use in the synthesis of erythromycin derivatives, involving a modified Heck reaction which employs less than six mole percent of palladium catalyst and no phosphine. With this modified Heck reaction, an O-alkenylaryl macrolide can be obtained in a much shorter reaction time than under conventional Heck reaction conditions. The modified Heck reaction can be utilized in a method for phosphine-free arylation of an O-allylic erythromycin derivative, in a method for preparing an O-alkenylaryl erythromycin A derivative, or in a method for preparing a 2',4"-hydroxyl protected 6-O-alkenylaryl erythromycin A derivative. A specific discussion of the methods follows, including a detailed description of representative erythromycin derivative starting materials, alkene formation and arylation.

The Erythromycin Derivatives

The starting materials for the modified Heck reaction are erythromycin derivatives. The terms "erythromycin derivative" or "erythromycin derivatives" refer to erythromycins A-D (shown in Formula I and Table 1) and derivatives thereof (exemplified by Formulae II–VI below).

More specifically, the term "erythromycin derivative" refers to the following types of erythromycins: those having a 9-keto group; those wherein the 9-keto group is converted into an oxime having either no substituents or a substituent in place of the oxime hydroxyl hydrogen; those wherein the 9-keto group is converted to a thioimine; and those wherein the 9-keto group is converted to a phosphoimide. Any of the above types may optionally having conventional protecting groups in place of the hydrogen of the 2' and 4" hydroxyl groups.

For example, derivatives may include substitutions for the C-2 through C-13 hydrogen, hydroxy, alkyl or alkoxyl substituents of erythromycins A-D, with different hydrogen, hydroxy, alkyl or alkoxyl substituents. Other examples of useful erythromycin derivatives are disclosed in U.S. Pat. Nos. 5,866,549; 5,872,229; 5,919,916; 5,932,710; 6,040,440; 6,075,011 and 6,124,269, the disclosures of which are hereby incorporated by reference.

The term "6-O-substituted erythromycin derivatives" as used herein refers to erythromycin 9-oxime derivatives or erythromycins wherein various substituents such as alkyl, alkenyl, aryl or alkenylaryl groups replace the hydrogen of the 6-hydroxyl group.

Presently preferred erythromycin derivatives may be described as follows.

An erythromycin derivative which may be utilized in the methods of the invention is represented by formula (II) below:

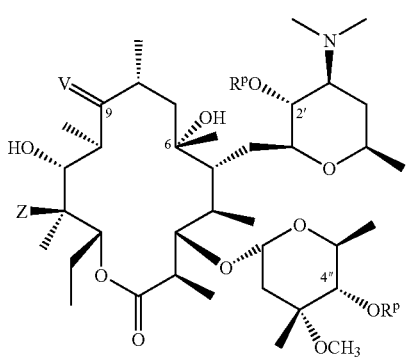
(II)

wherein:
$R^p$ is independently a hydrogen or a hydroxyl-protecting group at each ocurrence;
V is selected from the group consisting of:
a) O
b) an oxime having the formula N—O—$R^2$; wherein
$R^2$ is selected from the group consisting of:
hydrogen,
a lower alkenyl group,
an aryl(lower alkyl) group, and
a substituted aryl(lower alkyl) group;
c) an oxime having the formula

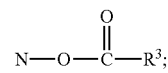

wherein
$R^3$ is selected from the group consisting of:
alkyl,
alkylaryl,
aryl, and
substituted aryl;
d) an oxime having the formula

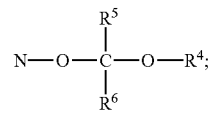

wherein
$R^4$ is selected from the group consisting of:
a lower alkyl group,
a cycloalkyl group,
an aryl group, and
an aryl(lower alkyl) group;
or $R^4$ and $R^5$ or $R^4$ and $R^6$ and the atoms to which they are attached are taken together form a 5- to 7-membered ring containing one oxygen atom; and
$R^5$ and $R^6$ are independently selected from the group consisting of:
a hydrogen atom,
a lower alkyl group,
an aryl group,
an aryl(lower alkyl) group;
or any pair of substituents selected from ($R^4$ and $R^5$), ($R^4$ and $R^6$) or ($R^5$ and $R^6$) and the atoms to which they are attached are taken together to form a 5- to 7-membered ring optionally containing one oxygen atom; provided that only one pair of substituents ($R^4$ and $R^5$), ($R^4$ and $R^6$) or ($R^5$ and $R^6$) may be taken together with the atoms to which they are attached to form a ring as defined above;
e) an oxime having the formula:

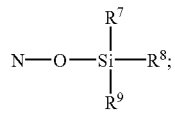

wherein $R^7$, $R^8$, and $R^9$ are independently selected at each occurrence from hydrogen, lower alkyl, aryl-substituted alkyl, aryl, cycloalkyl, and lower alkenyl;

f)

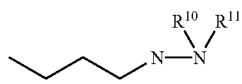

wherein $R^{10}$ and $R^{11}$ are independently selected at each occurrence from hydrogen, alkyl, or nitrogen-protecting group, or $R^{10}$ and $R^{11}$ taken together form a 5- to 7-membered cycloalkyl ring;

g)

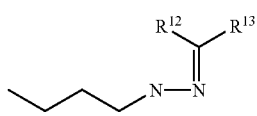

wherein $R^{12}$ and $R^{13}$ are independently selected at each occurrence from hydrogen, alkyl or a nitrogen-protecting group; or $R^{12}$ and $R^{13}$ taken together form a 5- to 7-membered cycloalkyl ring;

h) a thioimine of the formula

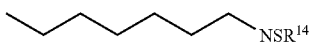

wherein $R^{14}$ selected from the group consisting of hydrogen, lower alkyl, aryl-substituted alkyl, aryl, cycloalkyl, and lower alkenyl; and i) a phosphoimide of the formula

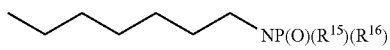

wherein $R^{15}$ and $R^{16}$ are each independently selected from the group consisting of hydrogen, lower alkyl, aryl-substituted alkyl, aryl, cycloalkyl, and lower alkenyl;

and Z is hydroxyl or a protected hydroxyl group.

Another useful erythromycin derivative is a 6-O-substituted erythromycin derivative, as represented by formula (III)

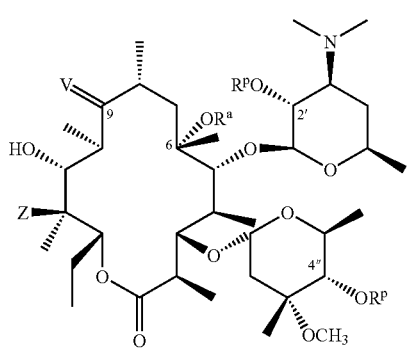

(III)

wherein $R^a$ is represented by the formula:

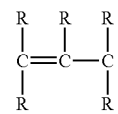

and wherein $R^p$, V and Z are as defined above; and R, at each occurrence, is independently selected from the group consisting of hydrogen, $C_1$–$C_{10}$ alkyl, halogen, aryl and substituted aryl.

The compounds of formula (III) may be optionally deprotected and deoximated to obtain compounds of formula (IV), also erythromycin derivatives which may be utilized in the methods of the present invention.

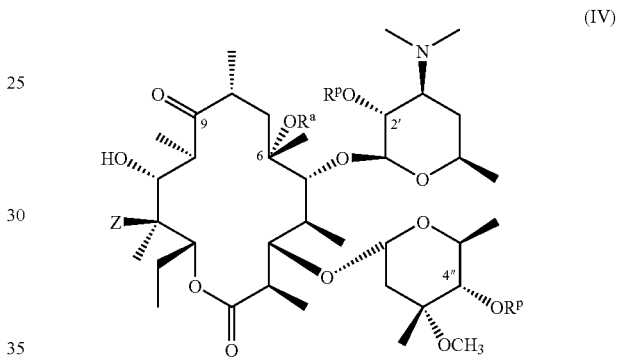

(IV)

wherein $R^p$, $R^a$ and Z are as defined above.

Another useful erythromycin derivative is of the structure V, shown below.

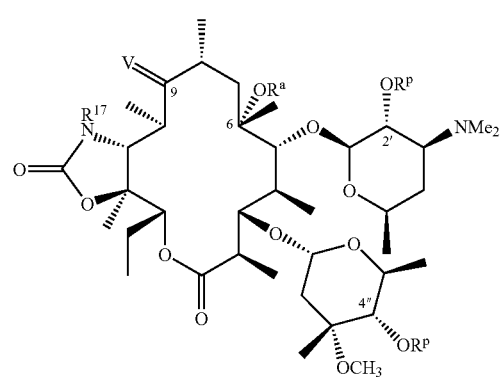

(V)

wherein $R^{17}$ is hydrogen or alkyl; and $R^p$, $R^a$ and V are as defined above.

The compounds of formulas (II), (III), (IV) and (V) are useful intermediates in the synthesis of macrolide antibiotics as described in the U.S. Pat. No. 5,866,549, represented by formula (VI).

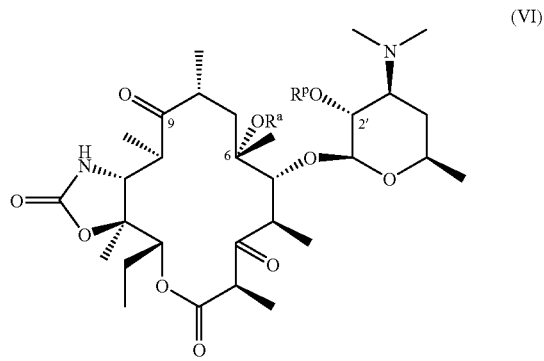

(VI)

wherein $R^p$ and $R^a$ are as defined above

Arylation

The arylation of the present invention is a modified Heck reaction, omitting phosphine reagents. The Heck reaction is well known, and is discussed in great detail in several review articles such as *Journal of Organometallic Chemistry*, vol. 576, pp. 16–22, (1999); *Chemical Society Reviews*, vol. 27, pp. 427–436, (1998); *Tetrahedron*, vol. 53 (22), pp. 7371–7395, (1997) and *Contemp. Org. Synth.*, vol. 3 (6), pp. 447–471, (1996) and references cited therein inter alia.

Surprisingly, the omission of phosphine reagents results in a high yield of product in a much shorter time than compared to the standard Heck conditions, as illustrated in Example 10 below. In addition to the advantage provided by this shorter reaction time, omission of the phosphine reagent decreases production costs and reduces unwanted side products.

For the practice of the method, any one of several different palladium catalysts may be utilized, such as palladium (II) acetate, palladium (II) chloride, palladium dibenzylideneacetone, dichlorobis(acetonitrile)palladium (II), dichlorobis(benzonitrile)palladium (II), dichlorodiamine palladium (II), palladium (II) acetylacetonate, palladium (II) bromide, palladium (II) cyanide, palladium (II) iodide, palladium oxide, palladium (II) nitrate hydrate, palladium (II) sulfate dihydrate, palladium (II) trifluoroacetate, tetraamine palladium (II) tetrachloropalladate and tetrakis(acetonitrile) palladium (II) tetrafluoroborate among others. $Pd(OAc)_2$ (palladium (II) acetate) is the presently preferred catalyst. Less than six mole percent of catalyst is all that is necessary to run the reaction. Preferably, the range of catalyst is from one to five mole percent, and a presently most preferred amount of catalyst is two mole percent.

Organic solvents such as dimethoxyethane, acetonitrile, N,N-dimethylformamide, N,N-dimethylacetamide, 1,3-dimethyl-3,4,5,6-tetrahydro-2(1H)-pyrimidinone, N-methylpyrrolidone, toluene, tetrahydrofuran, and combinations thereof may be employed for the modified Heck reaction. N,N-Dimethylformamide is the presently preferred solvent for the modified Heck reaction. Preferably, about 5–10 ml of solvent is used per gram of alkene.

The arylation is done in the absence of a conventional phosphine reagent. This omission of phosphine is presently preferred, since phosphine-free palladium in DMF provides increased yields and shorter reaction times.

The modified Heck reaction may be run at a temperature of from about 90° C. to about 120° C.; and most preferably at a temperature of 110° C. Typical reaction time is from 120 minutes to eighteen hours, though the reaction is usually complete within three hours.

Inorganic bases such as $K_2CO_3$, KOAc, NaOAc, $Li_2CO_3$, $LiHCO_3$, $Ag_2CO_3$, $Cs_2CO_3$, $KHCO_3$, $K_2CO_3$, $Na_2CO_3$ and $NaHCO_3$, among others, are presently preferred. A presently most preferred base is sodium bicarbonate. From about 1.5 to about 3 equivalents of base per equivalent of starting material will be useful in the methods of the present invention.

The arylating agent may be an aryl halide such as bromobenzene, 4-bromochlorobenzene, 4-bromopyridine, 8-bromoquinoline, 4-bromoanisole or 1-bromo-4-fluorobenzene, among others. A presently preferred aryl halide is 3-bromoquinoline. A presently preferred ratio for the amount of arylating agent to alkene starting material (to be arylated) is 1.2:1.

When running the modified Heck reaction, additives such as phase transfer reagents may be utilized such as tetrabutyl ammonium chloride, tetrabutyl ammonium sulfate, tetrabutylammonium iodide and tetrabutyl ammonium bromide, among others. A presently preferred phase transfer reagent is tetrabutyl ammonium chloride. A presently preferred ratio for the amount of phase transfer reagent to alkene starting material is 1:1.

In the examples which follow, the modified Heck reaction has been utilized to modify the 6-O-allyl group. However, it is expected that this reaction should be equally advantageous for derivatizations at other positions on erythromycin derivatives such as at C-11 or C-12.

A discussion of the various steps which may be utilized in conjunction with the methods of the present invention follows.

2'- and 4''-Hydroxyl Protection/Deprotection

The 2'- and 4''-hydroxyl groups of the erythromycin derivatives may be protected by reaction with a suitable hydroxyl protecting reagent in an aprotic solvent. Typical hydroxyl-protecting groups include, but are not limited to, alkylating agents, acetylating agents, silylating agents and acid anhydrides, among others. For example, acetic anhydride, propionic anhydride, benzoic anhydride, benzyl chloroformate, or a trialkyl silyl chloride are among the suitable hydroxyl protecting reagents.

Examples of aprotic solvents are dichloromethane, chloroform, N,N-dimethylformamide, tetrahydrofuran, N-methylpyrrolidinone, dimethylsulfoxide, N,N-dimethylacetamide, hexamethyl phosphoric triamide, ether, 1,2-dimethoxyethane, tetrahydrofuran, acetonitrile, ethyl acetate, acetone and combinations thereof.

Protection of 2'- and 4''-hydroxyl groups of erythromycin derivatives may be accomplished sequentially or simultaneously, with the same or two different reagents. A particularly preferred group for protecting the hydroxyl groups is the benzoate protecting group. Benzoylation of the hydroxyl group is typically accomplished by treating the erythromycin derivative with a benzoylating agent, such as benzoyl halide or benzoyl anhydride.

The deprotection of the 2'- and 4''-hydroxyl groups is carried out in accordance with methods described in the literature, for example as described in detail in *Protective Groups in Organic Synthesis*, 3rd Edition, by T. Greene and P. Wuts, published by John Wiley & Sons in New York in 1999. When the protecting group is an ester such as acetate, propionate or benzoate, the compound may be deprotected by treatment with ethanol or methanol. When the group to be removed is a trialkylsilyl group, the compound may be deprotected by treatment with a source of fluoride in tetrahydrofuran or acetonitrile.

The Methods, in General

As set forth in detail herein, it is possible to perform the reactions of the methods of the present invention in a single pot, although it will be appreciated that the described method can be practiced in multiple pots. A "single pot" process is a process that can be performed in a single reaction vessel. It will be appreciated by those of ordinary skill that single pot processes provide certain advantages over multiple pot processes. For example, single pot processes require less handling and/or transfer of components, thereby reducing the risk of accident or mistake. Single pot processes also tend to be less expensive than multiple pot processes as a result of the reduction in handling and transfer of reaction ingredients.

After completion of the reactions of the methods of the present invention, the desired compound may be recovered or isolated from the reaction mixture by conventional means, for example any one or any appropriate combination of the following steps: adjustment of the pH of the reaction mixture; concentration of the reaction mixture, e.g. by evaporating off the solvent under reduced pressure; separating, e.g. by filtration, of the reaction residue; or, if no crystalline precipitate is thereby produced, extracting the mixture with two immiscible solvents and then evaporating the solvent from the extract. If desired, the resulting product may be further purified by conventional techniques, for example recrystallization or the various chromatography techniques such as column chromatography or preparative thin layer chromatography.

It is contemplated that other ingredients such as solvents, catalysts, diluents, and other materials may also be present in the reaction mixture if desired, as long as the added extraneous materials do not materially change the nature of the reaction described above, but are added to promote the reaction, suppress side reactions, or improve the purification step of the synthesis.

The compounds which may be prepared by the methods of the present invention include compounds which may possess immunosuppressive, anti-microbial, anti-fungal, anti-viral, anti-inflammatory, and anti-proliferative activity, and may possess the ability to reverse chemotherapeutic drug resistance.

Compounds synthesized by the methods of the present invention may also find utility in the treatment of autoimmune diseases, such as rheumatoid arthritis, Hashimoto's thyroiditis, multiple sclerosis, myasthenia gravis, type I diabetes, uveitis, allergic encephalomyelitis, glomerulonephritis, among others.

Further uses may include the treatment and prophylaxis of inflammatory and hyperproliferative skin diseases and cutaneous manifestations of immunologically-medicated illnesses, such as psoriasis, atopical dermatitis, and Epidermolysis bullosa. Further instances where a compound of the invention may be useful include various eye diseases (autoimmune and otherwise) such as ocular pemphigus, Scleritis, and Graves' opthalmopathy among others.

These Examples are presented to describe preferred embodiments and utilities of the methods of the invention and are not meant to limit the invention unless otherwise stated in the claims appended hereto.

EXAMPLE 1

6-O-(3-(3-quinolyl)-2-propen-1-yl) erythromycin 2', 4"-dibenzoate was synthesized by a phosphine-free Heck reaction in the following manner.

To a vessel was charged 2 g 6-O-allyl 2', 4"-dibenzoate erythromycin A (2 mmol, obtained by allylation of an erythromycin derivative, as disclosed in WO 00/78773), 0.5 g 3-bromoquinoline (2.5 mmol), 0.28 g tetrabutylammonium chloride (2 mmol), 0.25 g sodium bicarbonate (3 mmol), Pd(OAc)$_2$ 30 mg (0.1 mmol), and 20 ml DMF. After degassing with N$_2$, the reaction mixture was stirred at 100° C. for 4 hours. 40 ml EtOAc and 40 ml water were then added. Next, the organic layer was separated and washed by 20 ml water twice. The resulting EtOAc solution was evaporated to residues and then 30 ml of acetonitrile was added. After stirring at 50° C. for 2 hours, the reaction mixture was cooled to room temperature. The solid was filtered and washed with 10 ml acetonitrile, dried under vacuum at 45° C. to give 1.24 g product 6-O-(3-(3-quinolyl)-2-propen-1-yl) erythromycin 2', 4"-dibenzoate, yield 55%.

EXAMPLE 2

6-O-(3-(3-quinolyl)-2-propen-1-yl) erythromycin 11,12-cyclic carbamate, 2', 4"-dibenzoate was synthesized by a phosphine-free Heck reaction in the following manner.

To a vessel was charged 2 g 6-O-propenylerythromycin 11,12-cyclic carbamate 2', 4"-dibenzoate (2 mmol, obtained by allylation of an erythromycin derivative, as disclosed in WO 00/78773), 0.5 g 3-bromoquinoline (2.4 mmol), 0.56 g tetrabutylammonium chloride (2 mmol), 0.25 g sodium bicarbonate (3 mmol), 10 mg palladium acetate (2% mmol), and 12 ml DMF. After degassing with N$_2$, the reaction mixture was stirred at 110° C. for 2.5 hours. Then, 25 ml IPAc and 10 ml distilled water were added and the organic layer was washed with 12 ml water twice. The IPAc solution was then passed through an 0.5 g FILTROL pad and rinsed with 5 ml IPAc. The combined IPAc solution was then concentrated to 10 ml, followed by addition of 10 ml of heptane and cooling to 4° C. for 16 hours. The solid was filtered and dried under vacuum at 45° C. to give 1.89 g product 6-O-(3-(3-quinolyl)-2-propen-1-yl) erythromycin 11,12-cyclic carbamate, 2', 4"-dibenzoate, yield 84%.

EXAMPLE 3

6-O-(3-(3-quinolyl)-2-propen-1-yl) erythromycin A oxime 2', 4",9-tribenzoate was synthesized by a phosphine-free Heck reaction in the following manner.

6-O-Allyl erythromycin A oxime 2', 4",9-tribenzoate (A, 1.10 g, MW 1101.3, 1.0 mmol, 1.0 equivalents, synthesized according to a procedure disclosed in WO 00/78773), 3-bromoquinoline (0.25 g, MW 208.1, 1.2 mmol, 1.2 equivalents), palladium acetate (5 mg, MW 224.5, 0.02 mmol, 0.02 equivalents), sodium bicarbonate (0.13 g, MW 84.0, 1.5 mmol, 1.5 equivalents), and tetrabutyl ammonium chloride (0.28 g, MW 277.9, 1.0 mmol, 1.0 equivalents) were charged to a 15 ml pressure tube and slurried in DMF (6 ml). The tube was sealed and the mixture was then heated to 110° C. with stirring. Upon heating, the slurry thinned and the light orange solution turned brown. After two hours, analysis by HPLC showed that the starting material had been consumed. The reaction mixture was then cooled to room temperature and diluted with 10 ml of water and 20 ml of isopropyl acetate. The layers were separated and the organic layer further diluted with 5 ml of isopropyl acetate and then washed with water (2×20 ml). Next, the organic layer was dried over sodium sulfate and the solvent stripped to a foam. The weight of the isolated solid 6-O-(3-(3-quinolyl)-2-propen-1-yl) erythromycin A oxime 2', 4'',9-tribenzoate B was 1.2 g. HPLC analysis indicated the presence of 3-bromoquinoline (9.3% relative to product), enol ether (5.4% relative to product), and regioisomer (7.8% relative to product).

Using the procedure described above, the modified Heck reactions were also conducted:

- on 6-O-allyl-2', 4''-O-dibenzoyl erythromycin A oxime (C) to form 6-O-(3-(3-quinolyl)-2-propen-1-yl)-2', 4''-O-dibenzoyl erythromycin A oxime;
- on 6-O-allyl-2', 4''-O-dibenzoyl-erythromycin A-9-(O-isopropoxycyclohexylketal) oxime (D) to form 6-O-(3-(3-quinolyl)-2-propen-1-yl)-2', 4''-O-dibenzoyl erythromycin A-9-(O-isopropoxycyclohexylketal) oxime;
- on 6-O-allyl-2', 4''-O-bis-trimethylsilyl-erythromycin A-9-(O-isopropoxycyclohexylketal) oxime (E) to form 6-O-(3-(3-quinolyl)-2-propen-1-yl)-2', 4''-O-bis-trimethylsilyl erythromycin A-9-(O-isopropoxycyclohexylketal) oxime;
- and on 6-O-allyl erythromycin A-9-(O-isopropoxycyclohexylketal) oxime (F) to form 6-O-(3-(3-quinolyl)-2-propen-1-yl) erythromycin A-9-(O-isopropoxycyclohexylketal) oxime;

and gave similar results.

Compounds C—F were also synthesized according to a procedure disclosed in WO 00/78773.

EXAMPLE 4

6-O-allyl erythromycin A-9-(diphenylphosphonimidyl) oxime 2', 4''-dibenzoate 2, starting material for a phosphine-free Heck reaction, was synthesized as follows.

A solution of $Ph_2PCl$ (0.8 ml, 2.2 equiv.) in $CH_2Cl_2$ (5 ml) was slowly charged from an addition funnel to a solution of imidazole (600 mg, 4.4 equiv.) in $CH_2Cl_2$ (15 ml) at 4° C. The addition rate was controlled so that the internal temperature did not exceed 5° C. The addition funnel was subsequently rinsed with a small amount of $CH_2Cl_2$ (2 ml), and the rinse was added to the cloudy white mixture. After 30 minutes of mixing at 0° C., a solution of 6-O-allyl erythromycin A-9-oxime 2', 4''-dibenzoate, macrolide 1 (synthesized according to a procedure disclosed in WO 00/78773, 1.994 g, 1.0 equiv.) in $CH_2Cl_2$ (5 ml) was charged in via an addition funnel while maintaining the internal temperature at not more than 5° C. The addition funnel was also rinsed with $CH_2Cl_2$ (3 ml). The resultant mixture was stirred at 0° C. for 30 minutes, at which point there was no starting material remain by HPLC and TLC analyses.

The crude reaction mixture was concentrated under reduced pressure to dryness. The residue was taken up in EtOAc (40 ml) and 20% aqueous $(NH_4)_2SO_4$ (20 ml). The organic layer was washed two more times with 20% aqueous $(NH_4)_2SO_4$ (2×20 ml), followed by a water wash (20 ml). The organic fraction was concentrated to furnish a white foam, 2.73 g. The material 2, 6-O-allyl erythromycin A-9-(diphenylphosphonimidyl) oxime 2', 4''-dibenzoate was used in the next step without further purification, and a quantitative yield was assumed for this step.

HPLC conditions: Zorbax Rx-C8 4×250 mm column, ambient temperature. FR=1.0 ml/min. λ=205 nm. Solution A=800:200:1 $H_2O$/MeCN/conc. $H_3PO_4$; Solution B=200:800:1 $H_2O$/MeCN/conc. $H_3PO_4$.

| Time (min.) | Solution A | Solution B |
| --- | --- | --- |
| 0 | 100% | 0% |
| 15 | 0% | 100% |
| 30 | 0% | 100% |

TLC eluent: 2:1 EtOAc/heptanes, visible by UV lamp or by p-anisaldehyde stain.

EXAMPLE 5

6-O-(3-(3-quinolyl)-2-propen-1-yl) erythromycin A-9-(diphenylphosphonimidyl)oxime 2', 4''-dibenzoate 3 was synthesized by a phosphine-free Heck reaction in the following manner.

To a reaction vessel containing macrolide 2 (6-O-allyl erythromycin A-9-(diphenylphosphonimidyl) oxime 2', 4''-dibenzoate, crude foam obtained according to the procedure of Example 4), $NaHCO_3$ (63 mg, 1.5 equiv.), and DMF (1.0 ml) was charged a solution of TBACl (139 mg in 2.0 ml DMF, 1.0 equiv.), followed by 3-bromoquinoline (82 µL, 1.2 equiv.), then a solution of the $Pd(OAc)_2$ (5.6 mg in 2.0 ml DMF, 5 mole percent). The reaction mixture was evacuated and purged several times with nitrogen, then heated to 100° C. After 8.25 hours, the mixture was cooled to ambient temperature.

The reaction mixture was then taken up in IPAc (20 ml). It was washed with $H_2O$ (10 ml), twice with 10% aqueous $NH_4Cl$ (2×10 ml), and once more with 5% aqueous NaCl (10 ml). The aqueous layers were combined then back-extracted with IPAc (20 ml). Since both organic layers contain product by HPLC analysis, they were combined and concentrated down to yield a residue. The residue foam was purified by silica gel chromatography (gradient of 2:1 to 7:3 to 3:1 EtOAc/heptanes mixtures). Due to the unstable properties of the phosphoimide functionality on silica gel, only 94 mg of a mixture was collected from the column. The desired product 6-O-(3-(3-quinolyl)-2-propen-1-yl) erythromycin A-9-(diphenylphosphonimidyl)oxime 2', 4''-dibenzoate 3 was present as the major component, with 80% PA purity. The desired molecular weight (MW 1307) was confirmed by LC-MS.

$^1$H-NMR: (300 MHz, in $CDCl_3$) 8.65 ppm (d, 1H), 8.10–7.25 (m, 22H), 7.12–6.93 (m, 3H), 6.27 (ddd, 1H), 6.06 (d, 1H), 5.30 (dd, 1H), 5.20–4.85 (m, 3H), 4.60–3.40 (m, 5H), 3.55 (s, 3H), 3.20 (s, 1H), 3.05–2.80 (m, 2H), 2.50 (d, 1H), 2.32 (s, 6H), 2.15–0.68 (m, 24H), 1.11 (s, 3H), 0.94 (d, 3H), 0.85 (d, 3H), 0.83 (d, 3H), 0.78 (d, 3H), 0.60 (d, 3H).

$^{13}$C-NMR: (75 MHz, in $CDCl_3$) 206.5 ppm, 174.8, 166.1, 165.5, 150.1, 149.5, 146.9, 136.5, 133.8, 133.6, 133.3, 132.5, 132.4, 131.7, 131.5, 131.3, 131.2, 131.1, 130.9, 130.7, 130.6, 130.2, 130.0, 129.9, 129.6, 129.3, 129.0, 128.5, 128.4, 128.2, 128.1, 128.0, 127.8, 127.4, 126.1, 99.9, 96.3, 90.3, 79.9, 79.3, 78.9, 78.6, 76.3, 74.4, 72.9, 72.7, 69.1, 67.2, 64.4, 63.7, 49.5, 44.0, 41.9, 41.7, 40.9, 38.3, 37.9, 37.6, 35.3, 31.6, 21.5, 21.3, 21.2, 18.4, 18.1, 16.2, 15.8, 15.0, 10.7, 9.5.

LC-MS conditions: Zorbax SB-C8 2.1×50 mm column, 25° C. FR=0.2 ml/min. λ=212–400 nm. Solvent A=MeCN;

solvent B=10 mM NH$_4$OAc/0.2% Formic acid. Interface temperature=220° C.

| Time (min.) | Solution A | Solution B |
|---|---|---|
| 0 | 40 | 60 |
| 8 | 80 | 20 |
| 24 | 80 | 20 |

HPLC conditions: Zorbax Rx-C8 4×250 mm column, ambient temperature. FR=1.5 ml/min. λ=235 nm. Solvent=60% MeCN in 23 mM aqueous PO$_4^{3-}$ (pH 4.4). Isocratic conditions, 25 minute run time.

EXAMPLE 6

6-O-allyl erythromycin A-9-phenylthioimine-2', 4"-dibenzoate 4, starting material for a phosphine-free Heck reaction, was synthesized as follows.

To a 25 ml 3-neck round bottom flask was charged 6-O-allyl erythromycin A-9-oxime 2', 4"-dibenzoate, macrolide 1 (synthesized according to a procedure disclosed in WO 00/78773, 997 mg, 1.0 equiv.) and PhSSPh (437 mg, 2.0 equiv.). After evacuating and purging the reaction vessel with nitrogen, the solids were dissolved in THF (5 ml) to give a pale yellow solution. PBu$_3$ was then added dropwise to the reaction mixture. The resultant bright yellow solution was stirred overnight at ambient temperature, then it was quenched by addition of a 5% aqueous Na$_2$CO$_3$ solution (15 ml). The product was extracted into IPAc (20 ml). The organic residue was purified by silica gel chromatography (gradient of 2:1 to 3:2 to 1:1 heptanes/EtOAc mixtures). The desired product 6-O-allyl erythromycin A-9-phenylthioimine-2', 4"-dibenzoate 4 was present as the major component in the material collected (887 mg), with greater than 80% PA purity. The desired molecular weight (MW 1088) was confirmed by LC-MS.

$^1$H-NMR: (300 MHz, in CDCl$_3$) 8.10–7.95 ppm (d, 3H), 7.65–7.23 (m, 11H), 7.12 (m, 1H), 5.77 (m, 1H), 5.20–4.75 (m, 4H), 4.51 (m, 1H), 4.10–3.50 (m, 4H), 3.55 (s, 3H), 3.18 (s, 1H), 3.15–2.70 (m, 4H), 2.48 (d, 1H), 2.33 (s, 6H), 2.0–0.68 (m, 30H), 1.56 (s, 3H), 1.10 (d, 3H), 1.04 (s, 3H), 0.93 (d, 3H).

$^{13}$C-NMR: (75 MHz, in CDCl$_3$) 180.9 ppm, 174.6, 166.1, 165.5, 139.2, 134.7, 133.3, 132.6, 130.9, 129.9, 129.6, 128.7, 128.4, 128.2, 125.5, 124.7, 116.9, 99.8, 96.3, 79.1, 78.9, 78.8, 78.6, 76.4, 74.1, 73.0, 72.7, 70.0, 67.3, 66.3, 63.8, 63.7, 49.5, 44.2, 40.9, 37.9, 37.8, 37.3, 36.5, 35.4, 31.7, 21.6, 21.4, 21.3, 21.2, 18.7, 18.4, 16.2, 16.1, 15.0, 10.5, 9.5.

HPLC conditions: same as for the identification of phosphoimide 2.

EXAMPLE 7

6-O-(3-(3-quinolyl)-2-propen-1-yl) erythromycin A-9-phenylthioimine 2', 4"-dibenzoate 5 was synthesized by a phosphine-free Heck reaction in the following manner.

To a reaction vessel containing macrolide 4 (6-O-allyl erythromycin A-9-phenylthioimine-2', 4"-dibenzoate, obtained according to the procedure of Example 6, 545 mg, 1.0 equiv.), NaHCO$_3$ (63 mg, 1.5 equiv.), and DMF (1.0 ml) was charged a solution of TBACl (139 mg in 2.0 ml DMF, 1.0 equiv.), followed by 3-bromoquinoline (82 μL, 1.2 equiv.), then a solution of the Pd(OAc)$_2$ (5.6 mg in 2.0 mL DMF, 5 mole percent). The reaction mixture was evacuated and purged several times with nitrogen, then it was heated to 100° C. After 8.25 hours, the mixture was cooled to ambient temperature.

The reaction mixture was taken up in IPAc (20 ml). It was washed with H$_2$O (10 ml), twice with 10% aqueous NH$_4$Cl (2×10 ml), and once more with 5% aqueous NaCl (10 ml). The residue foam was purified by silica gel chromatography (gradient of 1:1 to 2:1 EtOAc/heptanes mixtures). The desired product 6-O-(3-(3-quinolyl)-2-propen-1-yl) erythromycin A-9-phenylthioimine 2', 4"-dibenzoate 5 was present as the major component in the material collected (367 mg, 79% PA), verified by comparison against an authentic sample by $^1$H-NMR, $^{13}$C-NMR, HPLC, and LC-MS.

$^1$H-NMR: (300 MHz, in CDCl$_3$) 8.67 ppm (d, 1H), 8.10–7.98 (m, 5H), 7.70–7.40 (m, 10H), 7.30–6.95 (m, 5H), 6.55 (m, 1H), 6.15 (d, 1H), 5.30 (dd, 1H), 5.20–4.90 (m, 3H), 4.52 (m, 1H), 4.25–3.45 (m, 4H), 3.57 (s, 3H), 3.30–2.30 (m, 4H), 2.34 (s, 6H), 2.15–0.70 (m, 30H), 1.65 (s, 3H), 0.96 (d, 3H), 0.87 (t, 3H), 0.79 (d, 3H).

$^{13}$C-NMR: (75 MHz, in CDCl$_3$) 181.0 ppm, 175.1, 166.1, 165.5, 150.1, 147.1, 139.2, 133.4, 132.7, 132.6, 130.9, 130.0, 129.9, 129.6, 129.2, 129.0, 128.9, 128.7, 128.5, 128.4, 128.2, 128.1, 128.0, 126.1, 125.4, 123.5, 99.8, 96.3, 90.4, 79.3, 79.2, 78.8, 78.7, 74.1, 74.0, 73.0, 72.6, 69.9, 67.3, 65.6, 63.8, 63.6, 49.5, 44.3, 40.9, 38.2, 37.9, 37.2, 36.6, 35.3, 31.7, 21.6, 21.5, 21.3, 21.2, 18.5, 16.2, 16.0, 15.0, 10.8, 9.5.

LC-MS conditions: Zorbax SB-C8 2.1×50 mm column, 35° C. FR=0.25 ml/min. λ=220–400 nm. Solvent A=MeCN; solvent B=10 mM NH$_4$OAc/0.2% Formic acid. Interface temperature=220° C.

| Time (min.) | Solution A | Solution B |
|---|---|---|
| 0 | 50 | 50 |
| 8 | 90 | 10 |
| 28 | 90 | 10 |

HPLC conditions: same as for the identification of phosphoimide 2.

EXAMPLE 8

6-O-(3-(3-quinolyl)-2-propen-1-yl) erythromycin A-9-(pivaloyl)oxime 2', 4"-dibenzoate was synthesized by a phosphine-free Heck reaction in the following manner.

To a vessel was charged 10.4 g erythromycin A-9-(pivaloyl)oxime 2', 4"-dibenzoate (synthesized according to a procedure disclosed in WO 00/78773) and 80 ml THF, which was distilled to 40 ml. Then 1.73 g t-butyl allyl carbonate; 22 mg palladium acetate and 85 mg dppb were added, and the mixture was refluxed for one hour. The resulting mixture was divided into two equal parts. One part was distilled to residue, and then 22 mg palladium acetate, 1.25 g 3-bromoquinoline, 1.61 g tetrabutylammonium bromide, 0.8 g sodium bicarbonate and 25 ml DMF were charged to the flask containing the crude residue. Subsequent to degassing with nitrogen, the solution was heated to 110° C. for five hours. After this time, 50 ml EtOAc and 30 ml water were added at room temperature and the organic layer was washed twice with 30 ml water. 90% yield of 6-O-(3-(3-quinolyl)-2-propen-1-yl) erythromycin A-9-(pivaloyl)oxime 2', 4"-dibenzoate was calculated.

EXAMPLE 9

6-O-(3-(3-quinolyl)-2-propen-1-yl) erythromycin A-9-(benzoyl)oxime 2', 4"-dibenzoate was synthesized by a phosphine-free Heck reaction in the following manner.

To a vessel was charged 10.6 g erythromycin A-9-(benzoyl)oxime 2', 4"-dibenzoate (synthesized according to a procedure disclosed in WO 00/78773) and 150 ml THF, which was distilled to 50 ml. Then 1.74 g t-butyl allyl carbonate; 22 mg palladium acetate and 86 mg dppb were added. The resulting mixture was refluxed for one hour, and then distilled to residue. Next, 44 mg palladium acetate, 2.6 g 3-bromoquinoline, 3.22 g tetrabutylammonium bromide, 1.59 g sodium bicarbonate and 50 ml DMF were charged to the flask containing the crude residue. Subsequent to degassing with nitrogen, the solution was heated to 110° C. for two hours. After this time, 50 ml EtOAc and 30 ml water were added at room temperature and the organic layer was washed twice with 30 ml water. 71% yield of 6-O-(3-(3-quinolyl)-2-propen-1-yl) erythromycin A-9-(benzoyl)oxime 2', 4"-dibenzoate was calculated.

EXAMPLE 10

To illustrate the surprising superiority of the phosphine-free Heck reaction over the Heck reaction for arylation of macrolides, the following comparative experiment was performed. The starting material and product are illustrated in Scheme 4.

Two reactions were run side-by-side to compare the phosphine and phosphine-free conditions. The Heck reaction (including phosphine reagent) is designated as reaction A, and the phosphine-free reaction of the present invention is designated as reaction B.

To each reaction vessel was charged 300 mg 6-O-propenylerythromycin 11, 12-cyclic carbamate 2'-,4"-dibenzoate (0.30 mmol, obtained by allylation of an erythromycin derivative, as disclosed in WP 00/78773), 37.5 mg NaHCO$_3$ (1.5 equiv.), DMF (0.5 ml to reaction A, 1.0 ml to reaction B), 3.12 mg PPh$_3$ in 0.5 ml DMF solution (4 mole percent, reaction A only), 82.8 mg TBACl in 1.0 ml DMF solution (1.0 equiv.), 48.5 µL 3-bromoquinoline (1.2 equiv.) and 1.34 mg Pd(OAc)$_2$ in 1.0 ml DMF solution (2 mole percent). The reaction mixtures were each heated to 110° C. and monitored by HPLC. Under Heck conditions, 80.7% PA of 6-O-(3-(3-quinolyl)-2-propen-1-yl) erythromycin 11,12-cyclic carbamate, 2'-, 4"-dibenzoate was obtained after six hours of reaction time. Unexpectedly, the phosphine-free Heck reaction of the present invention gave 83.2% PA of 6-O-(3-(3-quinolyl)-2-propen-1-yl) erythromycin 11, 12-cyclic carbamate, 2'-, 4"-dibenzoate after only three hours of reaction time.

All references cited are hereby incorporated by reference.

The present invention is illustrated by way of the foregoing description and examples. The foregoing description is intended as a non-limiting illustration, since many variations will become apparent to those skilled in the art in view thereof. It is intended that all such variations within the scope and spirit of the appended claims be embraced thereby.

Changes can be made in the composition, operation and arrangement of the method of the present invention described herein without departing from the concept and scope of the invention as defined in the following claims:

We claim:

1. A method of preparing a 2', 4"-hydroxyl protected 6-O-alkenylarylerythromycin A derivative comprising the steps of:
   protecting the 2'-hydroxyl and 4"-hydroxyl groups of a 6-hydroxyl, 2'-hydroxyl, 4"-hydroxyl erythromycin A derivative with at least one hydroxyl-protecting agent to form a 6-hydroxyl, 2', 4"-hydroxyl protected erythromycin A derivative;
   allylating the C-6 hydroxyl of said 6-hydroxyl, 2', 4"-hydroxyl protected erythromycin A derivative with an allylating agent to form a 6-O-allyl, 2', 4"-hydroxyl protected erythromycin A derivative;
   arylating said 6-O-allyl, 2', 4"-hydroxyl protected erythromycin A derivative with an arylating agent in the presence of an inorganic base, a phase transfer catalyst and less than six mole percent of a palladium catalyst in an organic solvent, without addition of a phosphine, at a temperature of from about 90° C. to about 120° C., for about 3 hours, to form a 2', 4"-hydroxyl protected 6-O-alkenylarylerythromycin A derivative; and then,
   optionally isolating said 2', 4"-hydroxyl protected 6-O-alkenylaryl erythromycin A derivative.

2. The method of claim 1 further comprising deprotecting the 2'- and 4"-hydroxyl protected positions of said 2', 4"-hydroxyl protected 6-O-alkenylarylerythromycin A derivative.

3. The method of claim 1 wherein said 2', 4"-hydroxyl protected 6-O-alkenylarylerythromycin A derivative is selected from the group consisting of 6-O-(3-(3-quinolyl)-2-propen-1-yl) erythromycin A oxime 2', 4", 9-tribenzoate, 6-O-(3-(3-quinolyl)-2-propen-1-yl)-2', 4"-O-dibenzoyl erythromycin A-9-(O-isopropoxycyclohexylketal) oxime, 6-O-(3-(3-quinolyl)-2-propen-1-yl)-2', 4"-O-bis-trimethylsilyl erythromycin A-9-(O-isopropoxycyclohexylketal) oxime, 6-O-(3-(3-quinolyl)-2-propen-1-yl) erythromycin A-9-(O-isopropoxycyclohexylketal) oxime and 6-O-(3-(3-quinolyl)-2-propen-1-yl) erythromycin A-9-(pivaloyl)oxime 2', 4"-dibenzoate.

4. The method of claim 1 wherein said at least one hydroxyl-protecting agent is selected from the group consisting of benzoic anhydride, propionic anhydride, acetic anhydride and trimethylsilyl chloride.

5. The method of claim 1 wherein said palladium catalyst is selected from the group consisting of palladium (II) acetate, palladium (II) chloride, palladium dibenzylideneacetone, dichlorobis(acetonitrile)palladium (II), dichlorobis(benzonitrile)palladium (II), dichlorodiamine palladium (II), palladium (II) acetylacetonate, palladium (II) bromide, palladium (II) cyanide, palladium (II) iodide, palladium oxide, palladium (II) nitrate hydrate, palladium (II) sulfate dihydrate, palladium (II) trifluoroacetate, tetraamine palladium (II) tetrachloropalladate, tetrakis(acetonitrile)palladium (II) tetrafluoroborate and combinations thereof.

6. The method of claim 1 wherein said organic solvent is selected from the group consisting of dimethoxyethane, acetonitrile, N,N-dimethylformamide, N,N-dimethylacetamide, 1,3-dimethyl-3,4,5,6-tetrahydro-2(1H)-pyrimidinone, N-methylpyrrolidone, toluene, tetrahydrofuran and combinations thereof.

7. The method of claim 1 wherein said inorganic base is selected from the group consisting of K$_2$CO$_3$, KOAc, NaOAc, Li$_2$CO$_3$, LiHCO$_3$, Ag$_2$CO$_3$, Cs$_2$CO$_3$, KHCO$_3$, K$_2$CO$_3$, Na$_2$CO$_3$ and NaHCO$_3$.

8. The method of claim 1 wherein said allylating agent is allyl t-butyl carbonate with a palladium catalyst.

9. The method of claim 1 wherein said phase transfer catalyst is selected from the group consisting of tetrabutyl ammonium chloride, tetrabutyl ammonium bromide, tetrabutyl ammonium iodide, tetrabutyl ammonium sulfate and combinations thereof.

10. A method for phosphine-free arylation of 6-O-propenyl erythromycin A comprising the steps of:
reacting the allyl group of 6-O-propenyl erythromycin A with 3-bromoquinoline in the presence of sodium bicarbonate, tetrabutyl ammonium chloride and less than six mole percent of $Pd(OAc)_2$ in N,N-dimethylformamide, without addition of a phosphine, at a temperature of from about 90° C. to about 120° C., for about 3 hours, to form 6-O-(3-(3-quinolyl)-2-propen-1-yl) erythromycin A; and then,
optionally isolating 6-O-(3-(3-quinolyl)-2-propen-1-yl) erythromycin A.

11. A method for a single pot allylation and arylation of erythromycin A comprising the steps of:
reacting the 6-hydroxyl of erythromycin A with allyl t-butyl carbonate and a palladium catalyst to form 6-O-propenyl erythromycin A;
reacting the allyl group of 6-O-propenyl erythromycin A with 3-bromoquinoline in the presence of sodium bicarbonate, tetrabutyl ammonium chloride and less than six mole percent of $Pd(OAc)_2$ catalyst in N,N-dimethylformamide, without addition of a phosphine, at a temperature of from about 90° C. to about 120° C., for about 3 hours, to form 6-O-(3-(3-quinolyl)-2-propen-1-yl) erythromycin A; and then,
optionally isolating 6-O-(3-(3-quinolyl)-2-propen-1-yl) erythromycin A.

12. A method of preparing 6-O-(3-(3-quinolyl)-2-propen-1-yl) erythromycin A-2', 4"-dibenzoate comprising the steps of:
protecting the 2'-hydroxyl and 4"-hydroxyl groups of erythromycin A with benzoic anhydride to form erythromycin A 2', 4"-dibenzoate;
allylating the C-6 hydroxyl of erythromycin A 2', 4"-dibenzoate with allyl t-butyl carbonate and a palladium catalyst to form 6-O-propenyl erythromycin A 2', 4"-dibenzoate;
arylating 6-O-propenyl erythromycin A 2', 4"-dibenzoate with 3-bromoquinoline in the presence of sodium bicarbonate, tetrabutyl ammonium chloride and less than six mole percent of $Pd(OAc)_2$ catalyst in N,N-dimethylformamide, without addition of a phosphine, at a temperature of from about 90° C. to about 120° C., for about 3 hours, to form 6-O-(3-(3-quinolyl)-2-propen-1-yl) erythromycin A-2', 4"-dibenzoate; and then,
optionally isolating 6-O-(3-(3-quinolyl)-2-propen-1-yl) erythromycin A-2', 4"-dibenzoate.

* * * * *